US005684180A

United States Patent [19]
Knöfel et al.

[11] Patent Number: 5,684,180
[45] Date of Patent: Nov. 4, 1997

[54] FRACTIONATION AND PURIFICATION OF AROMATIC POLYAMINE MIXTURES AND THE USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,567

[22] Filed: Mar. 28, 1996

[30] Foreign Application Priority Data

Apr. 7, 1995 [DE] Germany ............ 195 13 269.6

[51] Int. Cl.⁶ ............................................. C07C 209/86
[52] U.S. Cl. .................. 560/347; 564/315; 564/331; 564/332; 564/333; 564/334; 564/437; 564/450; 564/451
[58] Field of Search .................... 564/315, 331, 564/332, 333, 334, 437, 450, 451; 560/347

[56] References Cited

U.S. PATENT DOCUMENTS

| | | | |
|---|---|---|---|
| 3,996,283 | 12/1976 | Knofel | 564/333 |
| 4,087,459 | 5/1978 | Knöfel et al. | 564/331 |
| 4,297,511 | 10/1981 | Biller | 564/331 |
| 4,924,028 | 5/1990 | Knofel et al. | 564/331 |
| 5,196,591 | 3/1993 | Knofel et al. | 564/331 |
| 5,359,141 | 10/1994 | Knofel et al. | 564/331 |

FOREIGN PATENT DOCUMENTS

| | | |
|---|---|---|
| 2238319 | 2/1973 | Germany . |
| 2811885 | 9/1978 | Germany . |

*Primary Examiner*—Richard L. Raymond
*Attorney, Agent, or Firm*—Joseph C. Gil

[57] ABSTRACT

The invention relates to a process for the fractionation and purification of aromatic polyamine mixtures and to the use thereof.

9 Claims, 4 Drawing Sheets

FRACTIONATION AND PURIFICATION OF AROMATIC POLYAMINE MIXTURES AND THE USE THEREOF

BACKGROUND OF THE INVENTION

The present invention relates to a process for the fractionation and purification of aromatic polyamine mixtures and to the use thereof.

The preparation of aromatic polyamines and polyamine mixtures, particularly of the diphenylmethane series, is described in numerous patent applications and patents, as is the use of these products. Outstanding importance is attached to the use of these products as raw materials for the preparation of isocyanates, usually by reaction of the polyamine mixtures with phosgene according to the generally conventional and well known methods.

In many cases, however, the resulting isocyanates and isocyanate mixtures are not obtained in the form and composition subsequently preferably used in the isocyanate stage but have to be converted beforehand to the appropriate form for use by means of sometimes elaborate working-up and separation processes. Suitable polyamine precursors which may be converted in a less elaborate manner to the isocyanate use forms are in many cases difficult to produce or unobtainable in terms of process technology, or economically unattractive.

An example is the production of 4,4'-diisocyanatodiphenylmethane which is important for the preparation of valuable polyurethane materials, the amine precursor of which may be obtained usually from aniline and formaldehyde only together with isomers, particularly the 2,4' isomers and more highly functional polyamines. Although these constituents are the basis for isocyanates which are also sought after, the separation of the crude isocyanates into the isocyanates and isocyanate mixtures suitable for subsequent use is not easy.

Initially, a proportion of the binuclear compounds is usually separated from the remainder. The 4,4'-diisocyanatodiphenylmethane from the binuclear fraction is then separated from the other isomers in a second distillation stage requiring many separation stages.

Even in recent times, the 2,4' isomer in the enriched form has gained increasing importance as a polyurethane raw material, but may be enriched compared with the 4,4' isomer and separated from the 2,2' isomer possibly present only by an elaborate distillation procedure.

Isomer separation methods or enrichment methods within the fraction of polynuclear homologues, or of polyfunctional amine constituents, and of isocyanates of the diphenylmethane series, are virtually unknown.

4,4'-Diaminodiphenylmethane is also attracting increasing interest as a raw material for di-(4-isocyanatocyclohexyl)methane, the form of 4,4'-diisocyanatodiphenylmethane hydrogenated on the nucleus, wherein the provision of suitable aromatic polyamine mixtures for the hydrogenation stage with the highest, possible content of 4,4'-diaminodiphenylmethane with simultaneously the smallest possible proportion of 2,4'-diaminodiphenylmethane is very expensive.

It is well known that amines may be separated in certain cases by partial conversion to their salts, wherein use may be made inter alia of the different base strengths. These are usually monoamines with very different base strengths.

Such disproportionation effects in two-phase systems have also already been described for aromatic polyamine mixtures, particularly of the diphenylmethane series (German Auslegeschriften 2,238,319 and 2,528,694).

As a result of the numerous components present in such a mixture, the amino groups of which hardly differ at all in terms of type (virtually all of them are arylamino groups), the effects are not particularly great and pronounced to be of interest for direct use with simple means.

The object was thus to provide a process which allows the purposeful production of aromatic polyamine mixtures of a purer, novel composition in an economic manner under mild conditions.

DESCRIPTION OF THE INVENTION

Figure 1:
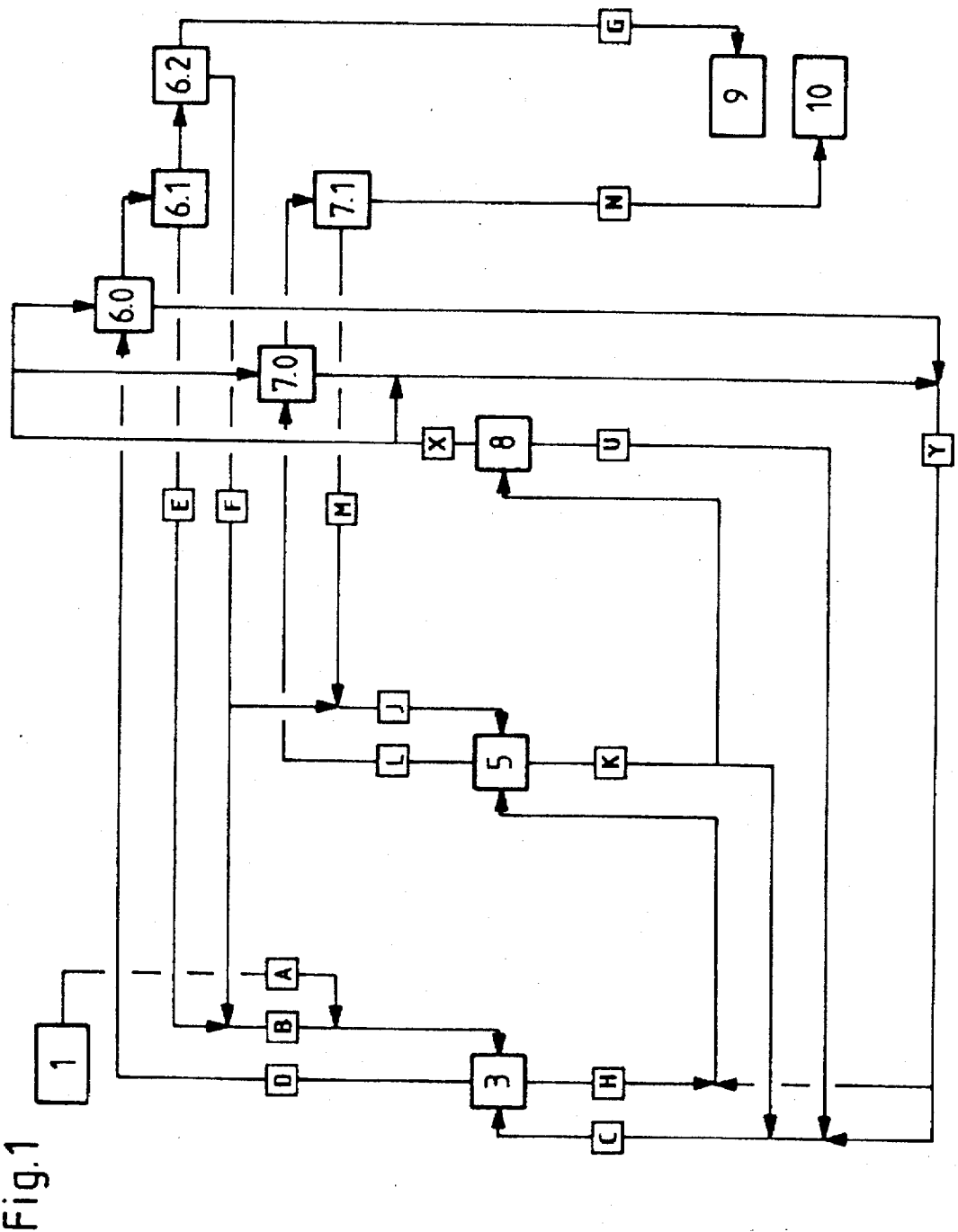
FIGS. 1 through 4 are flow diagrams of various embodiments of the present invention.

The above object could be achieved by the process according to the invention which achieves a surprisingly good separating efficiency during the fractionation of aromatic polyamine mixtures, particularly of the diphenylmethane series, and in terms of its effect thereby far exceeds the known effects of the prior art.

Other polyamine mixtures of varying composition are obtained during the fractionation of aromatic polyamine mixtures according to the invention. These derived polyamine mixtures may be those that are obtainable only at great expense by known synthesis routes. They may also be polyamine mixtures which are more suitable for a simplified preparation of isocyanates than the well known polyamine mixtures that are technically easy to prepare in that they, for example, anticipate in the amine stage the isomer separations that are difficult to perform in the isocyanate stage. Such mixtures may also be completely novel polyamine mixtures, because they cannot be prepared according to the prior art, which lead to completely new types of isocyanates.

On the other hand, the process according to the invention may be used to obtain product fractions conforming with the standard or the starting polyamines from any, i.e. also from recovered polyamine mixtures that differ from the originally used polyamines or isocyanates in terms of contamination or non-random, i.e. selective losses in the case of individual components during recovery from the originally used polyamines or isocyanates.

Finally, the process according to the invention may be used to co-fractionate synthesis-dependent secondary products and intermediates unwanted in the end product and to deplete them in one product fraction and enrich them accordingly in another, and optionally to expel them in an individual fraction.

The present invention is a broadly applicable process, by means of which the object of fractionating and purifying aromatic di- and polyamine mixtures, in particular of the diphenylmethane series, may be achieved.

The present invention provides a process for the fractionation and purification of aromatic polyamine mixtures, particularly polyamine mixtures of the diphenylmethane series, which is characterized in that a) the polyamine starting mixture (A) is distributed in a two-phase system comprising (i) a hydrophobic solvent phase (B) which is composed substantially of hydrophobic solvent and optionally an aromatic auxiliary amine that is virtually insoluble in water and under normal pressure has a boiling point at least 20° C. below the boiling point of the lowest boiling component of the starting mixture and at least 20° C. above the boiling point of the solvent, and optionally of polyamine, and (ii) an aqueous phase (C) comprising substantially water, a strong acid and auxiliary amine present at least partially in the salt form, and optionally polyamines present at least partially in the salt form, with the assistance of an extraction stage (3) operating on the countercurrent principle with mixing of the phases, by introducing the starting polyamine mixture via the organic phase (B), into the extraction stage (3), and at least partially separating the organic phase (D) leaving the extraction stage (3), optionally after passing through a wash stage (6.0) in a multistage distillation (6.1), (6.2) into a first fraction (E) reused in extraction stage (3) and substantially composed of hydrophobic solvent and optionally auxiliary amine, a second fraction (F), substantially composed of auxiliary amine and optionally hydrophobic solvent and a distillation residue (G), substantially composed of a first polyamine fraction and the aqueous phase (H) leaving the extraction stage is passed, b) optionally at least partially via an intermediate extraction stage (4), c) into an extraction stage (5), in which the aqueous phase is extracted according to the countercurrent principle with a solvent phase (J) composed of solvent and auxiliary amine, and the aqueous phase (K) depleted in polyarylamine results, which is passed d) optionally at least partially via an intermediate distillation stage (8) and then combined with the optionally remaining remainder of (K) and is reused e) as stream (C), in which the stated aqueous phase, f) optionally at least partially via an upstream extraction stage (2)

g) is introduced into extraction stage (3), optionally after the addition of auxiliary amine and/or water, and the h) the organic phase (L) obtained in extraction stage (5) is at least partially split by distillation (7.1) into a distillate (M) comprising auxiliary amine and solvent and a distillation residue (N) composed of a second polyamine fraction, whereupon the distillate (M) is combined with at least a proportion of the distillate (F) obtained in distillation stage (6.2) and is then returned to extraction stage (5) and there used again.

The numbers and capital letters above and in the description which follows refer to elements and streams in the drawings.

Preferably, the process according to the invention is performed in such a manner that the aqueous phase (H) arising in extraction stage (3) is at least partially extracted in an intermediate extraction stage (4) operating according to the countercurrent principle using an organic phase (O) as the extraction agent which is composed, in addition to hydrophobic solvent, of auxiliary amine and optionally polyamine, the latter preferably with a composition of the second partial product (N) and preferably introduced as a partial quantity of stream (L), the organic phase (P) arising in process stage (4) is introduced into the stream (B) and thus into extraction stage (3) and the resultant aqueous phase (Q) is introduced into extraction stage (5).

Particularly preferably, the process according to the invention is performed in such a manner that before being re-used, the aqueous phase (K) leaving extraction stage (5) is freed at least partially from a proportion (X) of the water contained therein by distillation (8), this water being used optionally for washing (6.0) that proportion of the organic phase (D) leaving extraction stage (3) fed to working-up by distillation (6.1), (6.2), and/or for washing (7.0) that proportion of the organic phase (L) leaving extraction stage (5) fed to working-up by distillation (7.1) for the purpose of removing acid traces and the water (Y) obtained in so doing is returned to the aqueous phase at a suitable place.

A further improved and thus preferred embodiment of the process according to the invention is achieved in that a partial quantity (D") of the organic phase (D) leaving extraction stage (3) is separated and extracted countercurrently in an upstream, preferably multistage, extraction stage (2) with at least a partial quantity, preferably with the entire stream of (C) and the partial stream (D") is calculated in such a manner that the polyamine contained in (D") is as far as possible transferred into the aqueous phase leaving the extraction unit (2), the said aqueous phase, optionally after the addition of water from stream (Y) and/or auxiliary amine and/or further aqueous phase from stream (C) is introduced into extraction stage (3) and the organic phase (R) arising in (2), which is substantially composed of hydrophobic solvent and optionally auxiliary amine, is also introduced into extraction stage (3) and, as a constituent of the organic phase (B), is used as a solvent for the starting polyamine (A). The auxiliary amine used is preferably aniline and the polyamine mixture of the diphenylmethane series used is preferably a polyamine mixture of the kind obtained during acid-catalyzed aniline/formaldehyde condensation.

The polyamine mixtures treated in this way, i.e. the fractions produced with the process according to the invention, are used for the production of the corresponding aromatic polyisocyanate mixtures and for the production of polyurethane plastics. Moreover, the fractions produced according to the process of the invention may be used for the production of the corresponding polyamines hydrogenated on the nucleus or as crosslinking agents and as epoxy curing agents. The corresponding polyisocyanates prepared from the fractionated polyamine mixtures are used preferably for the production of polyurethane foams.

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (3) with a two-phase system comprising (i) a hydrophobic solvent phase (B) which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) consisting essentially of water, a strong acid and auxiliary amine present at least in part in the salt form, and optionally polyamines present at least in part in the salt form, with said first extraction sage (3) operating on the countercurrent principle, and wherein said polyamine starting mixture (A) is introduced into said first extraction stage with said hydrophobic solvent phase (B), with a first aqueous phase (H) and a first organic phase (D) exiting said first extraction stage (3), b) distilling said first organic phase (D) in a multi-stage distillation (6.1), (6.2) into i) a first fraction (E) consisting essentially of hydrophobic solvent and optionally auxiliary amine,
  ii) a second fraction (F) consisting essentially of auxiliary amine and optionally hydrophobic solvent, and
  iii) a distillation residue (G) consisting essentially of a first polyamine fraction,
c) extracting said first aqueous phase (H) in a second extraction stage (5) with a solvent phase (J) consisting essentially of hydrophobic solvent and auxiliary amine, said second extraction stage (5) operating on the countercurrent principle, with i) a second aqueous phase (K), said second aqueous phase (K) being reduced in amine content and ii) a second organic phase (L) exiting said second extraction stage (5),
d) separating at least a portion of said second organic phase (L) in a distillation stage (7.1) into
  i) a first distillate (M) consisting essentially of hydrophobic solvent and auxiliary amine, and
  ii) a distillation residue (N) consisting essentially of a second polyamine fraction,
e) recycling said second aqueous phase (K) as at least a portion of stream (C), and
f) combining said first distillate (M) with a least a portion of said second fraction (F) to form solvent phase (J).

Starting mixtures are, for example, technical grade arylamine mixtures, of the kind obtained during production from the starting compounds or of the kind obtained during recovery.

Examples of starting arylamine mixtures, for the fractionation and purification of which the process according to the invention is particularly suitable, are 1. Polyamine mixtures of the diphenylmethane series, of the kind produced during the condensation and acid-catalyzed rearrangement of aniline with formaldehyde,
2. Polyamine mixtures of the diphenylmethane series, of the kind obtained during acid-catalyzed condensation of substituted anilines with formaldehyde,
3. Polyamine mixtures of the diphenylmethane series, of the kind obtained during mixed condensation of substituted anilines with one another and/or aniline with formaldehyde,
4. Polyamine mixtures of the diphenylmethane series, of the kind obtained during the condensation, including mixed condensation, of substituted anilines and/or aniline with aldehydes and/or ketones,
5. Polyamine mixtures of the diphenylmethane series of the kind produced during the nitration and subsequent reduction of di- and/or polyarylmethanes and/or substituted di- and/or polyarylmethanes; the term polyarylmethanes here means in particular the benzyl homologues of diphenylmethane,
6. Polyamine mixtures of the diphenylmethane series, of the kind produced during the condensation of monoarylmonoamines (for example aniline, substituted anilines) and/or monoaryldiamines (phenylenediamines, substituted phenylenediamines) with aldehydes, ketones, particularly formaldehyde, and acid-catalyzed rearrangement, and
7. Polyamine mixtures of the triphenylmethane series, of the kind produced, for example during the nitration and subsequent reduction of triphenylmethane, particularly alkyl-substituted triphenylmethanes and its polynuclear homologues, particularly benzyl homologues.

The hydrophobic solvents used are inert solvents with a boiling point in the range from 30° to 280° C., preferably from 80° to 200° C., such as, for example, chlorobenzene, dichlorobenzene, benzene, toluene, ethylbenzene, cumene, xylene, dichloroethane, chloroform and carbon tetrachloride. Xylenes i.e. technical grade xylene mixtures, particularly o-xylene, toluene, ethylbenzene, cumene and chlorobenzene, are preferably used. The solvents used are preferably those having good solvating power for the polyamine mixtures used.

The acids used are water-soluble protonic acids with a pKA value below 2.5, preferably below 1.5. Examples thereof are hydrochloric acid, hydrobromic acid, sulfuric acid, trifluoroacetic acid, methanesulphonic acid or phosphoric acid. Hydrochloric acid and methanesulphonic acid are preferably used. The acids mentioned may also be used in mixture with acid or neutral salts of such acids, such as, for example the corresponding ammonium salts or also the corresponding alkali salts. The acids mentioned are not used in the free form but are present in the circuit system according to the invention in the form of the corresponding ammonium salts of the bases situated in the aqueous circuit system. They are generally polyamine mixtures of the kind of the starting mixtures and/or the auxiliary amines used.

Monoarylamines such as, for example aniline and/or aniline derivatives alkyl-substituted on the nucleus and/or on the nitrogen, are generally used as the auxiliary amine. Primary anilines are preferably used; aniline is particularly preferred.

The process according to the invention may be performed both batchwise and continuously. A preferred embodiment is the continuous method of operation. The process is performed in all stages under the natural pressure of the system and preferably in an inert gas atmosphere (nitrogen).

The process according to the invention may be repeated with each of the resulting product fractions in order to increase the enrichment or corresponding depletion effect.

Figure 2:
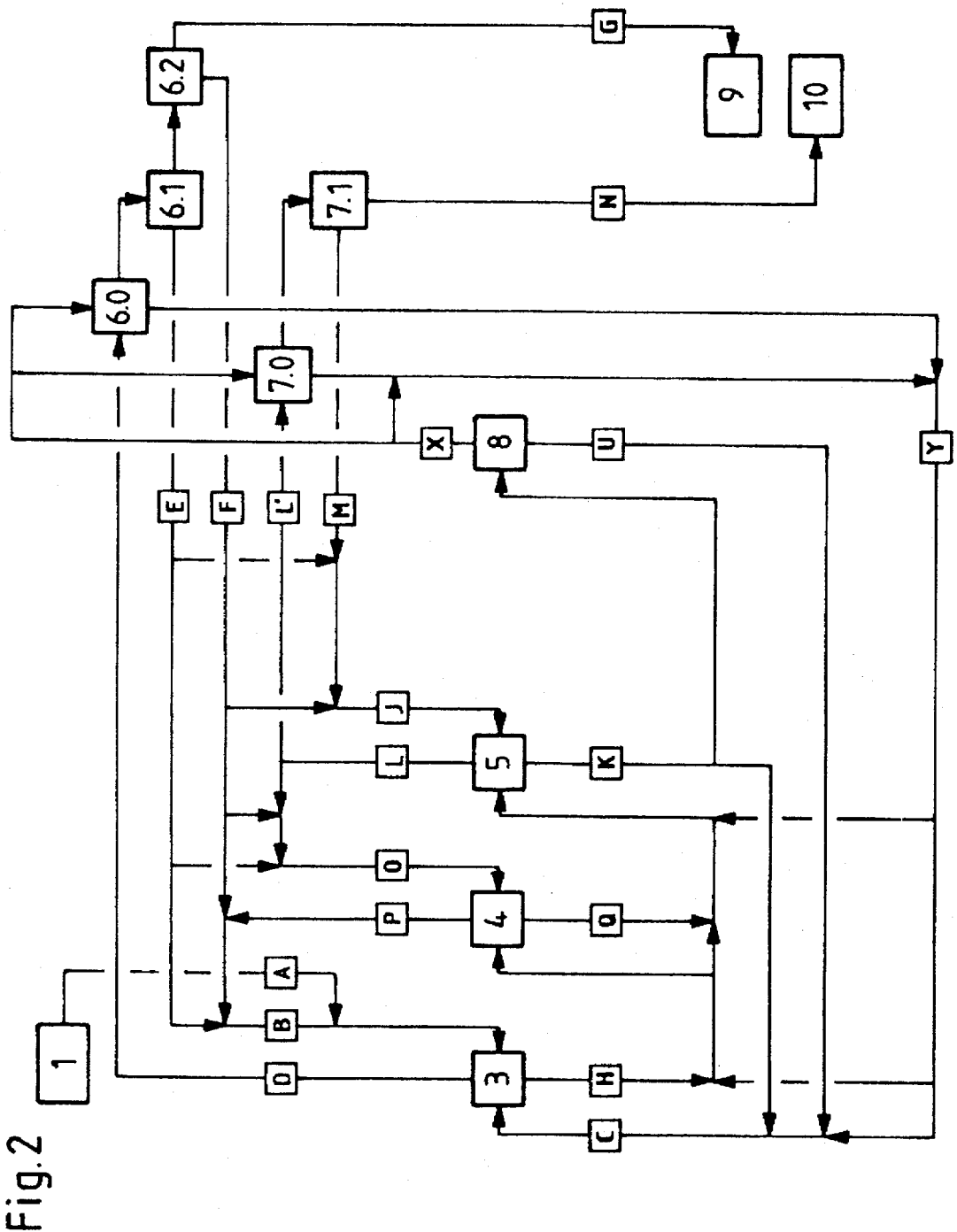
Figure 3:
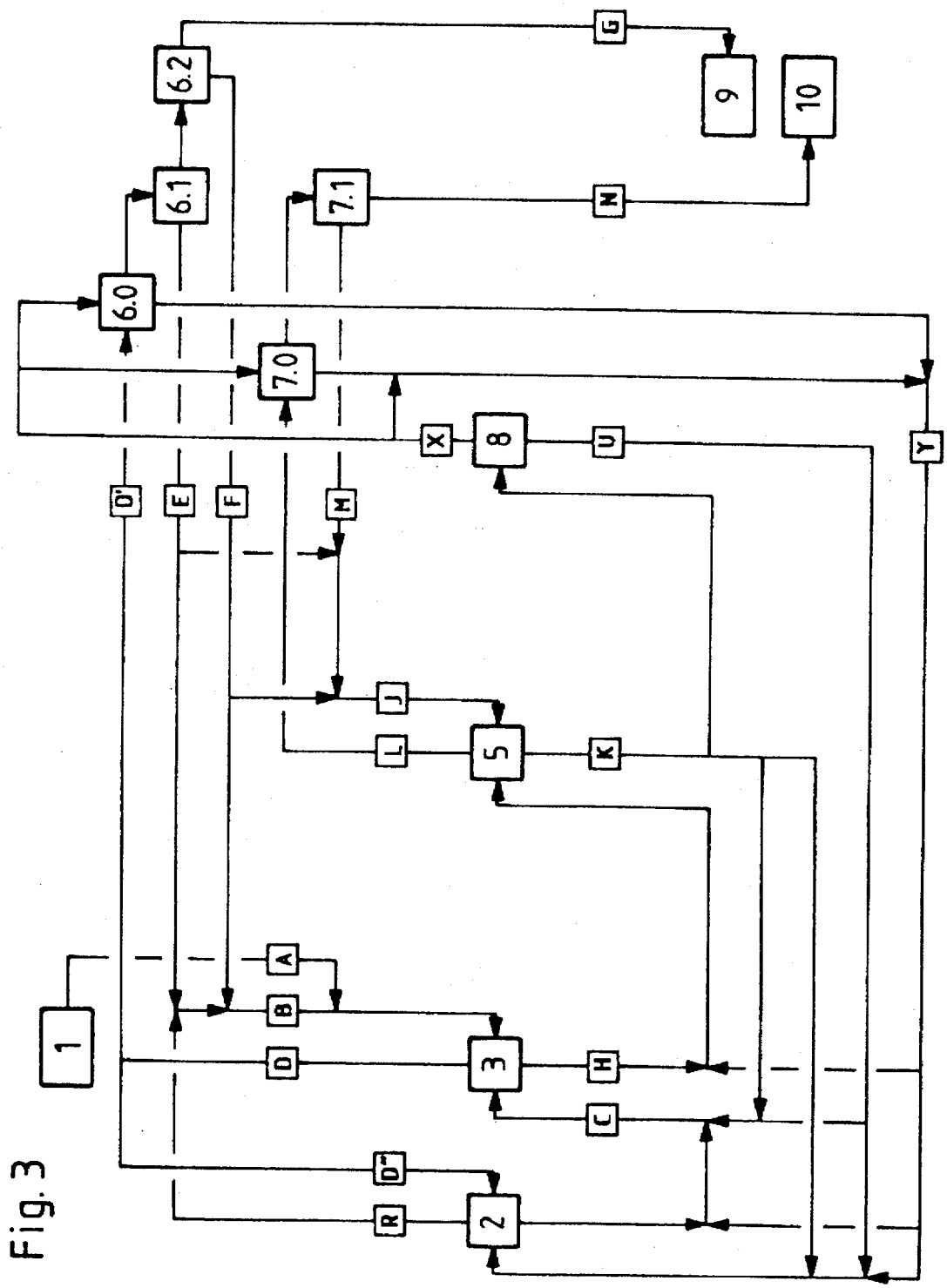
Figure 4:
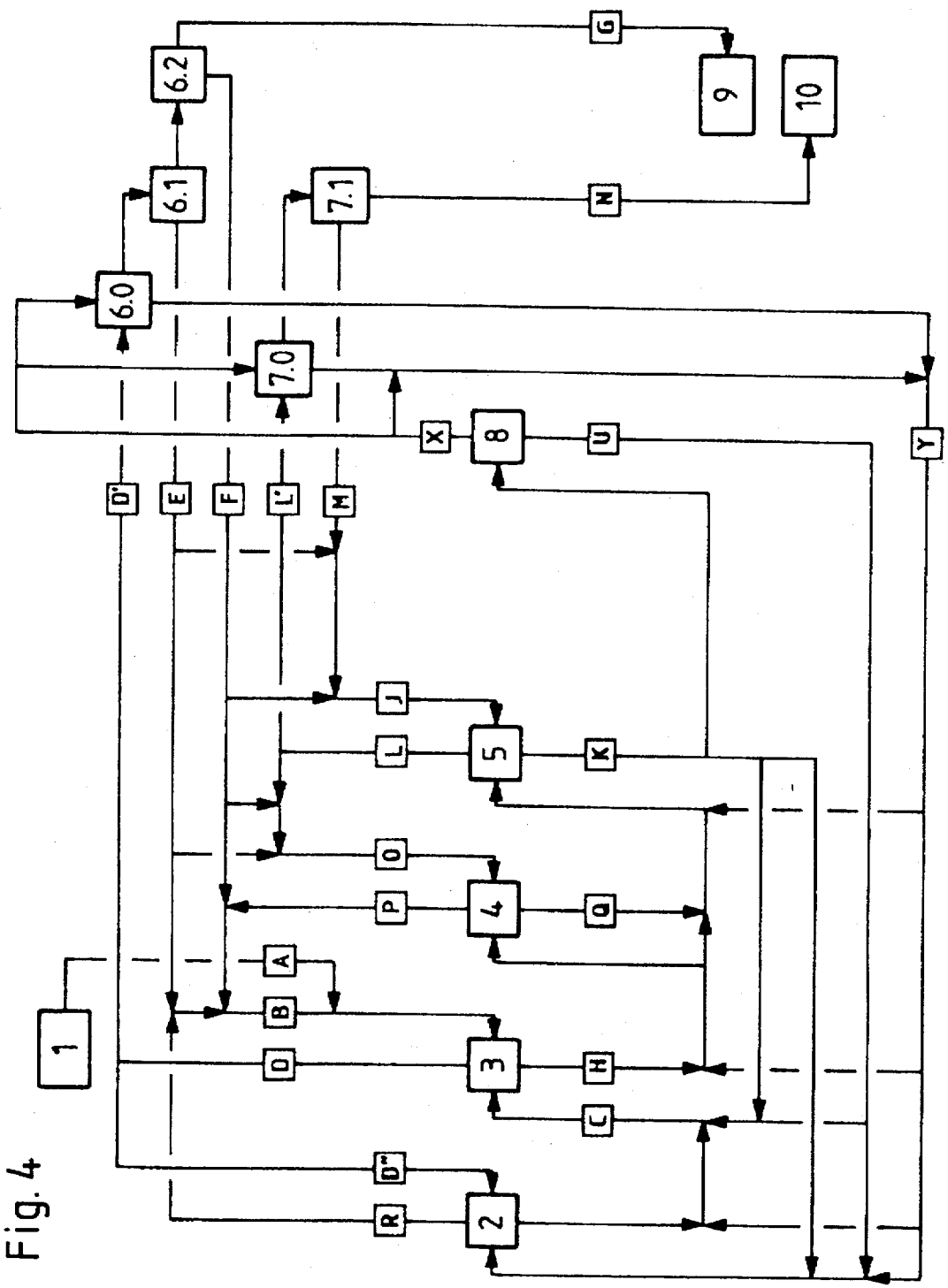

The process according to the invention may be performed with two (FIG. 1 ), with three (FIG. 2 and FIG. 3) or with four (FIG. 4) extraction stages.

The flow diagrams shown in FIGS. 1–4 serve to explain the process according to the invention in more detail. The references in these figures have the following meanings:

(1) a tank for the starting arylamine mixture
(2) an upstream extraction stage
(3) a first extraction stage
(4) an (intermediate) second extraction stage
(5) a (final) third extraction stage
(6) a working-up stage comprising
  (6.0) a wash stage
  (6.1) a first distillation stage of a multistage distillation
  (6.2) a final distillation stage of a multistage distillation
(7) a further working-up stage comprising
  (7.0) a wash stage
  (7.1) a distillation stage
(8) a water evaporator
(9) a tank for a process product
(10) a tank for a further process product.

The reference symbols A-U, X and Y denote the streams to which reference is made below in the examples.

The upstream extraction stage (2) is designed preferably as a multistage extractor. In the simplest case, extraction stage (3) is a single-stage mixer-separator unit, but multistage extraction units are preferably used here. In the simplest case, the optionally interposed extraction stage (4) is also a mixer-separator unit, but multistage extraction units are preferably used in this case too. The final extraction stage (5) is generally designed as a multistage extractor.

The working-up stages (6) and (7) serve to separate the polyamine fractions which are obtained as distillation residues and are isolated as process products (G) and (N) in the tanks (9) and (10), and for the recovery of the hydrophobic solvent used and of the auxiliary amine used as distillates.

It has proved convenient to remove residual traces of acid from the organic phases (D) or (D') and (L) or (L') fed to the distillation stages by extraction with water in upstream wash stages (6.0) and (7.0) before they are treated by distillation.

The actual working-up stage (6) generally comprises an at least two-stage multistage distillation, the first stage of which (6.1) yields a hydrophobic solvent as distillate (E) from which polyarylamine has been removed and which is depleted in auxiliary amine in comparison with the inflow product (D) or (D'), and the final stage of which (6.2) yields an auxiliary amine as distillate (F) from which polyarylamine has been removed and which is depleted in hydrophobic solvent in comparison with (D) or (D').

The complete separation of hydrophobic solvent and auxiliary amine by distillation is not necessary when performing the process according to the invention.

In addition, the first polyamine fraction of the starting mixture (A) contained in stream (D) or (D') is obtained as distillation bottom product (G) in the final distillation stage (6.2).

In the simplest case, the working-up stage (7) comprises a distillation column (7.1) which is designed such that the hydrophobic solvent and auxiliary amine are jointly largely separated as distillate (M) from the polyamine fraction (N) contained in the inflow to (6).

Preferably, however, the working-up stage (7) of the process according to the invention is also designed as a multistage distillation on account of the improved use of energy.

The distillation stage (8) is a device with which water can be removed by distillation from the aqueous phase of the system or from a partial stream of the aqueous phase. Such a stage is not necessary in principle for performing the process according to the invention, but because of the resulting advantages, the embodiments including a water distillation stage (8) are preferred.

The aqueous phase containing the acid is virtually a closed circuit system, so stage (8) may, in principle, be inserted in any position of this circuit system. The position of stage (8) following extraction stage (5) and before entry to extraction stage (2) or (3) is the most advantageous and therefore the preferred embodiment.

The quantity of water removed (X), optionally after being divided up into partial streams and differently used, is returned to the system at a suitable location in the form of stream (Y) as a whole or in partial streams, so that an extended and optionally branched inherently closed aqueous circuit system is produced.

This system also includes the wash stages (6.0) and/or (7.0). The latter are extraction stages operating in one or more stages on the counter-current principle. In wash stage (6.0), the organic phase (D) or (D') is freed from residual traces of acid with a partial stream of (X), and in wash stage (7.0) the organic phase (L) or (L') is freed from residual traces of acid with the use of another partial stream of water (X).

The distillate (X) contaminated with hydrophobic solvent and auxiliary amine is highly suitable for wash stages (6.0) and (7.0). The resulting wash waters generally have a very much lower acid concentration than the actual acid circuit, so these may be recycled without difficulty in the form of stream (Y) or its partial streams; optionally, a partial quantity of distillate of (X) may be fed past the wash stages after (Y) and used to control the varying water content of the aqueous phase in the individual extraction stages.

The virtually quantitative circulation of the acid used allows the use of expensive acids such as for example methanesulphonic acid which in turn, because of its reduced corrosion tendency, permits the use of inexpensive materials in the apparatus of the process according to the invention.

It has proved advantageous to define the acid content of the aqueous phase, independently of the varying amine content occurring in the aqueous phase of a two-phase system, by means of a so-called "molarity". "Molarity" is defined as the theoretical concentration of 100% protonated amine (i.e. same number of acid and amine equivalents) in a volume of aqueous phase reduced mathematically by the proportion of unprotonated amine according to the formula:

$$\text{"Molarity"} = \frac{\text{mol of 100\% protonated amine}}{\text{vol. of aqueous phase} - \text{vol. of unprotonated amine}}$$

The molarity thus defined may assume values of up to 6 and is purposefully varied in this range depending on the (in this case, product-related) separation task on which the relevant embodiment is based.

It may also be advantageous within an embodiment of the process according to the invention to operate the individual process stages through which the aqueous phase passes, particularly the extraction stages (2) to (5), with a different molarity in the aqueous phase by removing or adding water from or to the aqueous phase between the individual stages.

The upper limit of this operating range is technically limited on the one hand by the increasing crystallization tendency of the amine salts with increasing concentration, particularly at high degrees of protonation, and on the other hand by the increasing mutual solubility of the phases in one another, particularly at low degrees of protonation.

The lower limit of this range is limited by economic factors by the decreasing acid content and hence the quantitative decrease in separating efficiency, i.e. in order to achieve outstanding qualitative separating efficiency without technical difficulties, an increasingly large volume of aqueous phase is required for the separation of a given quantity of amine as the molarity falls.

The degree of protonation represents the ratio of acid equivalents to amine equivalents.

According to one variant of the process of the invention, the feeding of the starting polyamine mixture (A) from the storage vessel (1) takes place by mixing with the stream (B), formed by the stream (E) from the first distillation stage (6.1) and composed of hydrophobic solvent and optionally auxiliary amine, and optionally a partial stream of distillate (F) from the second distillation stage (6.2).

Once (A) has been added, the content of arylamine, composed of starting polyamine and auxiliary amine, in stream (B) is generally 10–80 wt. %, preferably 15–60 wt. %. Once (A) has been added, the content of starting polyamine in stream (B) is generally 5–60 wt. %, preferably 10–40 wt. %.

In the extractor (3), the stream (B), to which (A) has been added, is passed countercurrently to the aqueous phase (C).

Stream (C) is generally composed of water, a strong protonic acid, auxiliary amine and optionally polyamine. The acid is present in the form of its salts dissolved in water with auxiliary amine and optionally with polyamine. The amino groups of auxiliary amine and optionally polyamine are always present in (C) in a stoichiometric excess relative to the acid.

The degree of protonation in (C) is generally 10–90%, for the aniline preferably used as auxiliary amine it is preferably 25–70%

The well-defined molarity of stream (C) measured and controlled within narrow limits for the relevant embodiment of the process according to the invention is purposefully varied over a wide range depending on the (in this case, product-related) separation task on which the relevant embodiment is based.

Generally, the aqueous phase (C) fed into the first extraction stage of the process according to the invention has a molarity of between 0.5 and 4.5.

In extraction stage (3), which is preferably operated in multiple stages, stream (B), to which (A) has been added, is passed countercurrently to the aqueous phase (C). During this operation, polyamine is transferred from the organic phase (B) into the aqueous phase, generally with an at least partial exchange of auxiliary amine in the opposite direction.

The acid is present in the aqueous phase (H) leaving extraction stage (3) as an aqueous solution of the ammonium salts thereof with polyamine and optionally auxiliary amine, which solution generally contains free polyamine, i.e. which is not bound as a salt, and optionally free auxiliary amine, i.e. which is not bound as a salt.

The starting polyamine (A) introduced into the extractor (3) together with the organic phase (B) is divided into the aqueous phase (H) leaving the extractor and the organic phase (D) leaving the extractor (4) (quantitative fractionation).

The quantitative division of the individual components of the starting polyamine mixture into the resulting aqueous phase (H) and the resulting organic phase (D) takes place under the conditions of the process of the invention with a surprisingly high selectivity such that the resulting product fractions have a different composition which, in certain circumstances, differs considerably from that of the starting polyamine mixture (qualitative fractionation).

For example, starting from the preferably used aniline formaldehyde condensation products, it was found that the ortho-isomer form(s) of the polyamine component contained in two or more isomer forms in the starting mixture is (are) usually relatively enriched in the organic phase (D) leaving separating stage (3); for example, 2,4'-diaminodiphenylmethane relative to 4,4'-diaminodiphenylmethane. Conversely, the resulting aqueous phase (H) is relatively depleted in the 2,4' isomer, whilst the 4,4' isomer is relatively enriched.

If several "ortho-isomers" are present in the starting polyamine, for example 2,2'- and 2,4'-diaminodiphenylmethane, then the "ortho-richer" 2,2' isomer is more greatly enriched in the organic phase (D) compared with the "ortho-poorer" 2,4' isomer, that latter itself being relatively enriched compared with the "even ortho-poorer" 4,4' isomer.

The enrichment and depletion effect found initially with the aniline formaldehyde condensation products of the diaminodiphenylmethane series was associated on a purely empirical-descriptive basis with the criterion of ortho and pare substitution. The derived characterization of the process products as "ortho-rich" and "ortho-poor" is relative, and was expressed by the term "degree of ortho-substitution".

The "degree of ortho-substitution" is defined as the ratio of ortho amino group/methylene group relationships to the total number of all the amino group relationships. This term can cover virtually all the isomer separations for polyamines which are produced from arylamines, including substituted arylamines, with carbonyl compounds in an aqueous acid medium.

Surprisingly, the same enrichment-depletion effect (classified according to degree of ortho-substitution) was also found for the well-characterized and analytically detectable isomeric trinuclear compounds from aniline/ formaldehyde condensation.

The same applies to the separation of condensation products prepared from formaldehyde with aniline and diaminoaryl compounds such as phenylene or alkyl-substituted phenylenediamines.

The polyamine mixtures mentioned hitherto, as a result of their production, possess amino groups which are virtually only in the ortho and/or para position relative to methylene groups.

Within one group of isomeric compounds, those with the higher degree of ortho substitution are usually enriched in the organic phase (D) during fractionation compared with the isomers with a lower degree of ortho substitution.

Polyamine mixtures, particularly of the diphenylmethane series including the relevant polynuclear homologues which are prepared according to other processes, for example, by nitration of diphenylmethane or methyldiphenylmethanes and subsequent reduction, possess, in addition to amino groups in ortho and para positions, other amino group/ methylene group relationships as a result of their production. The process according to the invention is equally effective for these polyamine mixtures.

For example, a polyamine mixture primarily comprising an isomer mixture of

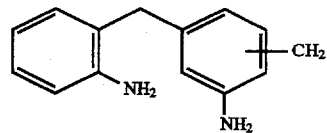

and

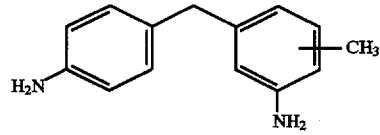

can be prepared from a mixture of 2- and 4-methyldiphenylmethane by nitration and subsequent reduction.

During the fractionation of such mixtures by means of the process of the invention, the 3,2' amino isomers in the organic phase (D) are enriched compared with the 3,4' amino isomers.

The criterion "ortho-rich" and "ortho-poor" or the degree of ortho-substitution in these polyamine mixtures no longer covers all the isomers and should therefore be applied mutatis mutandis in that, instead of the terms "in the ortho position" and "in the para position", the isomers are classified into those with a smaller (=ortho) and those with a larger (=para) spatial distance between the amino groups (usually situated on different six-membered rings) and the methylene bridge or between the amino groups themselves.

A further class of aromatic polyamine mixtures which can be fractionated very effectively by means of the process according to the invention are the polyamines of triphenylmethane and its polynuclear homologues, preferably benzyl homologues, of the kind produced, for example by nitration and subsequent reduction of the corresponding hydrocarbon mixtures.

During the fractionation of technical grade polyamine mixtures of the last-stated classes of substances I. Mixed condensation products of mono- and diaminoaryl compounds with formaldehyde or, generally, carbonyl compounds, II. Polyamine mixtures from processes by nitration and subsequent reduction of diphenylmethane and preferably substituted, particularly alkyl-substituted, diphenylmethanes and the relevant homologues, and III. Polyamine mixtures from processes by nitration and subsequent reduction of triphenylmethane and preferably substituted, particularly alkyl-substituted, triphenylmethanes and the relevant polynuclear benzyl homologues a further surprising selectivity was found in addition to the pure isomer separation.

Polyamine mixtures of the stated substance classes I to III contain or may contain components in which at least one aryl nucleus per molecule bears more than one, usually two, amino groups. These components may be the preferred components of the polyamine mixture without necessarily being the main products in quantitative terms, due to the process.

In order to improve the characterization of such components, the term "degree of amino substitution" is used, which primarily characterizes the number of amino groups of one component in relation to the number of aryl nuclei.

For aniline and its condensation products with formaldehyde, this expression is always 1.0, for phenylenediamine and its condensation products always 2.0. For pure mixed condensates, the value of 1.5 is obtained for the diphenylmethane isomers and values of between >1.0 and <2.0 are obtained for the polynuclear homologues. If the term "degree of amino substitution" is used statistically to characterize technical grade polyamine mixtures, values of between 1.0 and 2.0 are likewise obtained.

When fractionating polyamine mixtures with a degree of amino substitution of >1.0 it was found that the components with a higher degree of amino substitution are relatively enriched in the aqueous phase arising in the actual separation stage, the enrichment being greater with increasing degree of amino substitution.

Irrespective of this, separation by the degree of ortho substitution is also effective here.

The process according to the invention thus also opens up the possibility for this class of substances of divorcing the production form of the raw materials (amine stage) and the use form of the end products (isocyanate stage) so that a separate optimization of both stages is facilitated to the extent of obtaining completely new isocyanate mixtures.

These "achievements" are supplemented by a further criterion of selectivity which was found during the fractionation of technical grade polyamine mixtures, particularly those with polynuclear homologues, and relates to the "nuclearity" of the polyamine mixtures.

The term "nuclearity" primarily expresses the number of aryl units of a component of an aromatic polyamine mixture. In the wider sense, the term nuclearity is used to express statistically a nuclearity of the total mixture for a polyamine mixture composed of numerous components with an individual, exact nuclearity.

Particularly surprisingly, it was found when fractionating polyamine mixtures with polynuclear components, particularly when fractionating technical grade mixtures of aniline/ formaldehyde condensation products, that the polynuclear components in the organic phase leaving the fractionation stage can purposefully be both relatively enriched and relatively depleted, depending on the molarity of the aqueous phase in extraction stage (3).

A high molarity of the aqueous phase in (3) within the stated molarity range leads to a relative depletion of polynuclear components in the organic phase (D) and consequently to a relative enrichment in the aqueous phase (H).

A low molarity of the aqueous phase in (3) within the stated molarity range leads to a relative enrichment of polynuclear components in the organic phase (D).

The surprising finding may be extended and refined to the extent that the relative enrichment and depletion also takes place amongst the polynuclear homologues themselves. In a technical grade mixture of diaminodiphenylmethane, for example, if the trinuclear components in one fraction are relatively enriched or depleted compared with the binuclear components, a relative enrichment or depletion of tetranuclear components compared with trinuclear components is also found, i.e. an even greater relative enrichment or depletion, and the same occurs with pentanuclear components compared with tetranuclear components etc.

As a result of this and the isomer separation taking place simultaneously and always in the direction of a relative increase in the "degree of ortho-substitution" in the organic phase (D), and as a result of the possibility of repeating the separation according to the invention with individual product fractions, optionally with modified process parameters, there are numerous possibilities, starting from well known and readily obtainable polyamine mixtures, of obtaining by means of the process of the invention less readily obtainable or completely novel, because hitherto unobtainable by the prior art, polyamines and hence polyisocyanates. This is particularly true of products of the diamino- and diisocyanato-diphenylmethane series and quite particularly for polyamine and polyisocyanate mixtures with an extremely high proportion of polynuclear components.

The enrichment and depletion usually becomes more effective with an increasing degree of protonation in the aqueous phase of the separation stage.

Moreover, the process according to the invention also proves to be generally effective for other polyamines of a similar structure. For example, the polyamine mixtures already mentioned which are obtained by nitration of di- and polyarylmethanes and subsequent reduction may also contain monoaminopolyarylmethane compounds or components in which one or more methylene groups have been converted by secondary reactions into keto- and/or hydroxymethylene groups and thus into unwanted secondary products.

Numerous incompletely rearranged intermediate compounds and secondary products may occur during the condensation of arylamines with carbonyl compounds. Most of these compounds usually undergo enrichment in one of the resulting fractions during the fractionation of the polyamine mixtures containing them, so that the effect can be used for separation and fractionation.

Such products may be optionally enriched in this way or may themselves be fractionated as purposefully produced polyamine mixtures, such as, for example, polyaminobenzophenones or aminobenzylarylamine mixtures.

The organic phase (D) leaving extraction stage (3) contains, inter alia, small quantities of acid, generally and depending on the process parameters in extraction stage (3), between 0.01 and 0.5 wt. %, which are removed advantageously before stream (D) is worked up by distillation.

In the simplest case, this takes place by neutralization with excess dilute aqueous bases, for example, dilute sodium hydroxide solution. The washing out of the acid or its amine salts from the organic phase with water is, however, preferred so that optionally only residual traces are removed by contact with dilute sodium hydroxide solution or by means of an ion exchanger.

The wash water used is removed from the aqueous acid circuit by means of a water evaporator and added thereto at a location suitable for processing purposes after passing through the wash stage(s) together with the acid.

The organic phase (D) or (D') is transferred to the at least two-stage distillation stage (6.1), (6.2), optionally after passing through the acid wash stage (6.0).

In the first distillation stage (6.1), a distillate (E) is separated which contains the majority, preferably almost the entire quantity of the hydrophobic solvent contained in (D) or (D') in addition to a proportion of the auxiliary amine contained therein. Generally, the distillate (E) contains <50% of auxiliary amine, preferably 15–30%.

In the final distillation stage (6.2), the remaining auxiliary amine, optionally in addition to the residual quantity of hydrophobic solvent, is separated as distillate (F) from the first partial product (G) obtained as a distillation bottom product and collected in process product tank (9). Generally, (F) contains <50% of hydrophobic solvent, preferably 15–30%.

The corresponding second process partial product is situated in the aqueous phase (H) leaving extraction stage (3).

In a multistage extraction stage (5) operated preferably at 80°–110° C., the second partial product is extracted in exchange for auxiliary amine from the aqueous phase (H), optionally after the addition of water to reduce molarity and optionally after the addition of auxiliary amine to reduce the degree of protonation, and in so doing is transferred to the organic phase (L).

The molarity of the aqueous phase used in (5) is preferably <2.5.

The degree of protonation of the aqueous phase used in (5) is preferably <60%.

The extraction agent (J) used is a mixture of hydrophobic solvent and auxiliary amine, which is composed substantially of distillate fraction (M) from distillation stage (7.1) and at least a partial quantity of distillate fraction (F) from distillation stage (6.2).

The weight ratio of auxiliary amine to solvent in (J) is generally between 0.5:1 and 3:1, preferably between 1:1 and 2:1.

The weight ratio of extraction agent (J) to aqueous phase is generally between 0.3:1 and 3:1, preferably between 0.7:1 and 2:1.

The organic phase (L) or (L') arising in (5) is fed to distillation stage (7.1), optionally after passing through wash stage (7.0) and/or optionally after removal of acid traces with dilute sodium hydroxide solution.

The separation by distillation of distillation residue (N) takes place in distillation stage (7.1), which residue is collected as a second partial product in process product tank (10).

Distillation stage (7.1) may comprise, for example, a single-stage evaporator which yields a distillate (M) in addition to the distillation residue (N).

The distillate (M) contains, in addition to auxiliary amine, the entire hydrophobic solvent from (L) or (L') and is used as extraction agent (J) after addition of at least a partial quantity of (F). For the general case that (F) contains hydrophobic solvent in addition to auxiliary amine, a corresponding equalization of hydrophobic solvent with respect to (E) is performed if necessary, i.e. to the organic circuit in order to obtain the first partial product (not shown).

The aqueous phase (K) arising in (5) is returned to extraction stage (3), preferably at least partially via a distillation stage (8), in which the water quantity (X) is removed from the aqueous phase.

The route via (8) is absolutely vital if extraction stage (3) is operated with a higher molarity of the aqueous phase than extraction stage (5). In this case, the at least proportional return feed of water (Y) to the aqueous acid circuit takes place after leaving stage (3) and before entering stage (5).

In principle, the aqueous phase (H) arising in process stage (3) may be fed directly or optionally via an intermediate stage (4) to extraction stage (5). As, however, the upper molarity range of extraction stage (3) much preferred for certain separation tasks lies above the preferred molarity range of extraction stage (5), a preferred embodiment of the process of the invention is to divorce the molarities from those in the various extraction stages by optionally removing water by distillation from the inherently closed system of the aqueous phase, at a suitable location, and adding it again at another suitable location.

With the aid of a water distillation stage (8), water is removed from the aqueous phase containing the acid, or from a partial stream of the aqueous phase, preferably after leaving extraction stage (5) and before re-use at the beginning of the process, this water being added again as a whole (Y) or in partial quantities at one or more locations before the aqueous phase enters extraction stage (5).

By means of this first variant of the process according to the invention, it is possible to achieve high levels of separation efficiency on fractionation of polyamine mixtures and to solve numerous separation problems satisfactorily.

Particularly in the first polyamine fraction (G), it is possible purposefully to vary and maximize the relative enrichment of the components preferably contained in this fraction.

The remaining proportion of these components remaining in the second polyamine fraction (N) cannot, however, be minimized in the same manner, but only relatively depleted to a variable extent down to a content, the lower limit of which is dependent upon the distribution equilibria characteristic of the particular process parameters of the polyamine components of (A) between the organic phase (B) on entering the extractor (3) and the aqueous phase (H) on leaving the extractor (3).

By adding proportions of the second polyamine fraction (N), preferably as a partial stream of (L), to the starting arylamine (A), the content thereof of components of (G) may be reduced relatively and thus, by means of the distribution equilibrium, reduced below the lower limit of these components achievable according to the first variant. The only marginal improvement in separation performance achieved in this manner may be sufficient for certain applications, but generally has a negative effect on the throughput of (A).

A second variant of the process according to the invention is more advantageous and preferred as an embodiment, in which, additionally in the second polyamine fraction (N), the relevant enrichment of the components preferably contained in this fraction can, largely independently of the first product fraction, be varied purposefully, by extracting the organic phase (H) arising in extraction stage (3), or at least a partial quantity thereof, in a downstream extraction stage (4) operating according to the countercurrent principle with an organic phase (O).

The organic phase (O) is generally composed, in addition to hydrophobic solvent, of auxiliary amine and/or polyamine, the latter preferably having the composition of the second partial process product (N).

Using an organic phase (O) without polyamine gives rise to a polyamine fraction in the aqueous phase (Q) leaving extraction stage (4), in which fraction the relative enrichment of the components preferably contained in this phase may purposefully be increased and maximized above the enrichment achieved in the aqueous phase (H), to the expense of the polyamine concentration in the aqueous phase (Q).

Having polyamine as a constituent of the organic phase (O) ensures that the phases (P) and (Q) leaving process stage (4) have a higher polyamine concentration, which is thus more advantageous in energy terms for performance of the process according to the invention than when an organic phase (O) is used without polyamine.

By means of the preferred use of a polyamine with the composition of the second partial product (N) as a constituent of the organic phase (O), it is also possible under these energetically advantageous favorable conditions to vary and maximize the relative enrichment of the polyamine components preferably contained in the aqueous phase (Q) leaving separation stage (4) and thus of the second polyamine fraction (N) by adjusting the equilibrium with self-intensification of the separation effect.

In the simplest and general case, the organic phase (O) is composed of at least a partial stream of stream (E) and optionally further auxiliary amine from stream (F). (O) is preferably composed of a partial stream of (E) and a partial quantity of stream (L), containing the polyamine mixture (N) optionally together with auxiliary amine and together with hydrophobic solvent.

The addition of hydrophobic solvent and auxiliary amine from other sources may optionally completely be dispensed with, such that the organic phase (O) consists exclusively of a partial quantity of (L).

This embodiment of the process according to the invention is particularly advantageous in terms of separation efficiency and energy balance and is thus particularly preferred when it can be used.

The molarity of the aqueous phase used in the downstream extraction stage (4) is generally at the same level as that in the aqueous phase (H) leaving extraction stage (3). It is, however, possible by adding water and optionally also auxiliary amine to the aqueous phase to modify both molarity and degree of protonation in order to improve the separation efficiency according to the process of extraction stage (4).

It is also possible in principle to increase the molarity of the aqueous phase in (4) by removing water.

The organic phase (P) arising in stage (4) is added to the organic phase (B) used in extraction stage (3).

The aqueous phase (Q) arising in stage (4) is introduced, optionally together with the remainder of (H) into extraction stage (5).

The quantity of hydrophobic solvent which is optionally removed from the solvent circuit of the second process product (N) by branching off a partial stream of (L) in order to form the extraction agent (O), is offset preferably by adding a partial quantity of (E) during formation of the organic phases (J).

The relative enrichment of the two resultant polyamine fractions may purposefully be varied and maximized with the second variant of the process according to the invention. In addition to this great qualitative versatility and efficiency, the second variant of the process also constitutes an energetically favorable embodiment, at least for the second polyamine fraction (N).

On the other hand, the expenditure of energy associated with obtaining the first polyamine fraction (G) increases more sharply in relative terms the lower is the quantitative proportion of (G), relative to the polyamine mixture (A) used, because the remaining polyamine content (G) in the organic phase (D) to be worked up by distillation correspondingly becomes ever smaller.

The effect is brought to bear in particular when the components separated with (G) are contained in the starting mixture (A) only at a low concentration and/or are enriched to a relatively high degree in the fraction (G), for example during the separation according to the invention of polyamine mixtures of the diphenylmethane series.

Additional, partial introduction of starting polyamine (A) into separation stage (3) via the aqueous phase does indeed generally increase the polyamine concentration in (D) and thus reduces energy input. However, when the process is performed according to the invention, this reduction is associated with degradation of the qualitative separation result in the first partial product (G) due to an equilibrium being established between the polyamine in the aqueous phase and the polyamine in the organic phase (D), such that this possibility may be used only to a subordinate extent or in those cases placing correspondingly low demands on the separation result.

The third variant of the process according to the invention is an improved embodiment in this respect. Starting from the first variant, this is extended in such a manner that the organic phase (D) leaving process stage (3) and containing the first partial product (G) in a reduced concentration compared the concentration of (A) in (B) is divided into a stream (D'), which is introduced into working up stage (6) with the aim of isolating the polyamine fraction (G), and into a stream (D").

Stream (D") is extracted in an upstream extraction stage (2) with at least a partial quantity, preferably with the entire quantity, of the aqueous phase (C) which is available for reuse.

The quantity of the stream (D") introduced into the extractor (2) is here calculated such that, on reaction with stream (C), the polyamines contained in the organic phase (D") are as far as possible, preferably virtually quantitatively, transferred into the aqueous phase leaving the extractor (2).

An increased molarity in the aqueous phase arising from process stage (8) of the process according to the invention and used in stage (2) favors and facilitates the transfer of polyamine from the organic phase (D") into the aqueous phase.

The residual content of polyamine in the organic phase (R) leaving process stage (2) is generally <5 wt. %, preferably <1 wt. %.

Moreover, the maximum admissible content of amine in (R) and in particular the content of polyamine is determined by the quality requirements arising from the particular separation task which are placed upon the process products, i.e. the quality of separation, in the case of variant 3 in particular on the partial process product (N). Compliance with the content of polyamine relevant to the quality of (N) is controlled within the context of technical circumstances using the available aqueous phase by measuring the partial stream (D").

In quantitative terms, it is advantageous to the process and in particular to the upstream process stage (2) for the ratio of (D") to (D') to tend towards higher values, i.e. for (D") to be present in larger quantities, if the quantity ratio of the polyamine fraction (G) to (N) becomes smaller, because (N) increases at the expense of (G). As the proportion of the polyamine fraction (N) increases, the quantity of the aqueous phase in circulation and thus available in (2) for the extraction of (D") also increases.

The organic phase (R) leaving process stage (2), which has been depleted in amine, in particular from which polyamine has virtually been removed, is added to the organic phase (B) and introduced together with this into process stage (3) as a solvent for starting polyamine (A).

In addition to the aqueous acid used, the aqueous phase leaving process stage (2) contains polyamine, the composition of which largely corresponds to that of the polyamine separated in (D) and isolated as fraction (G), and optionally auxiliary amine.

In the simplest case, the aqueous phase leaving process stage (2) is added directly as stream (C) to process stage (3); further aqueous phase and/or water and/or auxiliary amine are optionally added prior to this.

It is also possible according to variant 3 to add a limited quantity of starting polyamine (A) to the aqueous phase without degrading qualitative separation efficiency (relative enrichment) in comparison with variant 1, but with improved quantitative efficiency (greater economic viability).

In a further, fourth variant, the upstream process stage (2) and its consequent advantages are combined with the embodiment of the process according to the invention described as variant 2, so bringing about a similar improvement with regard to the first partial product as described in variant 3. Performance of process stage (2) may be further facilitated and simplified by the requirement concerning the residual polyamine content of the organic phase (R) arising in (2) being less strict, since the disadvantageous effects of an increased polyamine content in (R) on the quality of the second partial process product (N) may be offset by the downstream extraction stage (4).

The polyamine content of the organic phase (R) leaving process stage (2) is thus generally <5 wt. %, preferably <3 wt. %.

The invention is further illustrated but is not intended to be limited by the following examples in which all parts and percentages are by weight unless otherwise specified.

EXAMPLE

Starting polyamine mixture (A) (2.000 kg/h) is mixed with stream (B) (5.961 kg/h) composed substantially of polyamine mixture, aniline and xylene.

Stream (B) is formed from stream (P) (3.205 kg/h), proportions of stream (E) and proportions of stream (F).

The resulting aqueous phase (streams A+B) has the following average composition

| Stream (A) + (B) | 40.5% polyarylamine |
| (7.961 kg/h) | 15.8% aniline |
| | 42.6% xylene |
| | <0.1% hydrogen chloride |
| | 1.1% water | and is passed countercurrently to stream (C) in a multistage extractor (3) at 90° C., which stream (C) has the following average composition:

| Stream (C) | 0.5% polyarylamine |
| (20.500 kg/h) | 15.8% aniline |
| | 3.7% hydrogen-chloride |
| | 80.0% water. |

The organic phase (D) leaving the extractor (3) has the following average composition:

| Stream (D) | 13.5% polyarylamine |
| (7.407 kg/h) | 38.3% aniline |
| | 45.8% xylene |
| | <0.1% hydrogen chloride |
| | 2.4% water. |

Stream (D) is washed with water in extractor (6.0). The wash water from (6.0) [and similarly from (7.0)] is combined with the aqueous phase at an appropriate point via stream (Y).

As a backup, stream (D) is washed with dilute sodium hydroxide solution. The aqueous phase is disposed of as effluent.

Once stream (D) has been washed and freed of acid residues, the majority of the xylene and a proportion of the aniline are removed in a first distillation stage (6.1). The distillate (stream E) is divided and introduced into process stages (3) and (5).

In the second distillation stage (6.2), the aniline and residual xylene are removed by distillation from the bottom phase of (6.1). The distillate is divided and introduced into process stages (3) and (5).

A polyamine mixture remains as the distillation bottom product of stage (6.2), which mixture is collected at approximately 1.0 kg/h in tank (9) as stream (G).

The aqueous phase (H) leaving the extractor (3) has the following average composition:

| Stream (H) | 11.1% polyarylamine |
| (21.054 kg/h) | 7.9% aniline |
| | 3.6% hydrogen chloride |
| | 77.4% water | and is passed countercurrently in a further multistage extractor (4) at 90° C. to an organic phase (O)[Stream (O) 3.071 kg/h], which is a partial quantity of organic phase (L).

The organic phase (P) arising in process stage (4) passes into stream (B).

| Stream (P) | 38.3% polyarylamine |
| (3.205 kg/h) | 19.5% aniline |
| | 39.7% xylene |
| | <0.1% hydrogen chloride |
| | 2.4% water |

The aqueous phase (Q) [Stream (Q) 20.919 kg/h] arising in (4) is passed countercurrently to stream (J) in a further multistage extractor (5) at 90° C.

| Stream (J) | 54.4% aniline |
| (7.916 kg/h) | 45.1% xylene |
| | 0.5% water |

Stream (J) is formed from distillate stream (M) from distillation stage (7.1) and appropriate proportions of distillate streams (E) and (F).

The organic phase (L) leaving the extractor (5) occurs with the following average composition:

| Stream (L) | 18.1% polyarylamine |
| (8.607 kg/h) | 37.9% aniline |
| | 41.5% xylene |
| | <0.1% hydrogen chloride |
| | 2.5% water. |

Stream (L) is divided into stream (O), which is introduced into extraction stage (4), and stream (L').

Before distillative working up in process stage (7.1), stream (L') is treated similarly to stream (D).

In the subsequent distillation stage (7.1), water, xylene and aniline are separated from the second polyamine fraction (N) which occurs as distillation bottom product.

The distillate arising in distillation stage (7.1) (optionally after mechanical separation of the water which condensed on cooling of the distillate) is used together with the remaining partial streams (E) and (F) to form extraction agent stream (J) and is used as such in the extraction stage.

Polyamine fraction (N) is collected at approximately 1.0 kg/h in tank (10) as a second partial product.

If necessary, water (stream X) is then removed by distillation from the aqueous phase (K) leaving extractor (5) in a water evaporator (8), which water is used together with the water optionally separated from the distillation streams from (6.1) and (7.1) to wash the organic phases in stages (6.0) and (7.0). The resultant wash waters are collected as stream (Y) and added to the aqueous phase arising in (8) to form stream (C).

The quantities of acid and water removed from the system in the backup neutralization stages on washing with sodium hydroxide are replaced from outside the system by addition to stream (C).

| Polyarylamine GC: | A [wt. %] | G [wt. %] | N [wt. %] |
|---|---|---|---|
| 2,2'-diaminodiphenylmethane | 0.22 | 0.44 | — |
| 2,4'-diaminodiphenylmethane | 7.12 | 14.24 | <0.1 |
| 4,4'-diaminodiphenylmethane | 60.20 | 20.90 | 99.50 |
| N-methyl-4,4'-diaminodiphenylmethane | 0.21 | 0.42 | — |
| Σ diaminodiphenylmethanes | 67.75 | 36.00 | 99.50 |
| Σ polynuclear polyamines | 32.25 | 64.00 | 0.50 |
| Quantity distribution | 100% | 50% | 50% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
   a) mixing the polyamine starting mixture in a first extraction stage with a two-phase system comprising
      (i) a hydrophobic solvent phase which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and
      (ii) an aqueous phase consisting essentially of water, a strong acid and auxiliary amine present at least in part in the salt form, and optionally polyamines present at least in part in the salt form,
      with said first extraction stage operating on the countercurrent principle, and wherein said polyamine starting mixture is introduced into said first extraction stage with said hydrophobic solvent phase, with a first aqueous phase and a first organic phase exiting said first extraction stage,
   b) distilling said first organic phase in a multi-stage distillation into
      i) a first fraction consisting essentially of hydrophobic solvent and optionally auxiliary amine,
      ii) a second fraction consisting essentially of auxiliary amine and optionally hydrophobic solvent, and
      iii) a distillation residue consisting essentially of a first polyamine fraction,
   c) extracting said first aqueous phase in a second extraction stage with a solvent phase consisting essentially of hydrophobic solvent and auxiliary amine, said second extraction stage operating on the countercurrent principle, with i) a second aqueous phase, said second aqueous phase being reduced in amine content and ii) a second organic phase exiting said second extraction stage,
   d) separating at least a portion of said second organic phase in a distillation stage into
      i) a first distillate consisting essentially of hydrophobic solvent and auxiliary amine, and
      ii) a distillation residue consisting essentially of a second polyamine fraction,
   e) recycling said second aqueous phase as at least a portion of said aqueous phase and
   h) combining said first distillate with at least a portion of said second fraction to form said solvent phase.

2. A process for the fractionation and purification of aromatic polyamine mixtures characterized in that
   a) the polyamine starting mixture (A) is distributed in a two-phase system comprising (i) a hydrophobic solvent phase (B) which is composed substantially of hydrophobic solvent and optionally an aromatic auxiliary amine that is virtually insoluble in water and under normal pressure has a boiling point at least 20° C. below the boiling point of the lowest boiling component of the starting mixture and at least 20° C. above the boiling point of the solvent, and optionally of polyamine, and (ii) an aqueous phase (C) comprising substantially water, a strong acid and auxiliary amine present at least partially in the salt form, and optionally polyamines present at least partially in the salt form, with the assistance of an extraction stage (3) operating on the countercurrent principle with mixing of the phases, by introducing the starting polyamine mixture via the organic phase (B), into extraction stage (3), and at least partially separating the organic phase (D) leaving extraction stage (3), optionally after passing through a wash stage (6.0), in a multistage distillation (6.1), (6.2) into a first fraction (E) reused in extraction stage (3) and substantially composed of hydrophobic solvent and optionally auxiliary amine, a second fraction (F), substantially composed of auxiliary amine and optionally hydrophobic solvent and a distillation residue (G), substantially composed of a first polyamine fraction and the aqueous phase (H) leaving the extraction stage is passed,
   b) optionally at least partially via an intermediate extraction stage (4),
   c) into an extraction stage (5), in which the aqueous phase is extracted according to the countercurrent principle with a solvent phase (J) composed of solvent and auxiliary amine, and the aqueous phase (K) depleted in polyarylamine results, which is passed
   d) optionally at least partially via an intermediate distillation stage (8) and then combined with the optionally remaining remainder of (K) and is reused
   e) as stream (C), in which the stated aqueous phase,
   f) optionally at least partially via an upstream extraction stage (2)

g) is introduced into extraction stage (3), optionally after the addition of auxiliary amine and/or water, and h) the organic phase (L) obtained in extraction stage (5) is at least partially split by distillation (7.1) into a distillate (M) comprising auxiliary amine and solvent and a distillation residue (N) composed of a second polyamine fraction, whereupon the distillate (M) is combined with at least a proportion of the distillate (F) obtained in distillation stage (6.2) and is then returned to extraction stage (5) and there used again.

3. The process of claim 2, wherein b) the aqueous phase (H) arising in extraction stage (3) is at least partially extracted in an intermediate extraction stage (4) operating according to the countercurrent principle using an organic phase (O) as the extraction agent which is composed, in addition to hydrophobic solvent, of auxiliary amine and optionally polyamine, the latter preferably with a composition of the second partial product (N) and preferably introduced as a partial quantity of stream (L), the organic phase (P) arising in process stage (4) is introduced into the stream (B) and thus into extraction stage (3) and the resultant aqueous phase (Q) is introduced into extraction stage (5).

4. The process of claim 2, wherein d) before being re-used, the aqueous phase (K) leaving extraction stage (5) is freed at least partially from a proportion (X) of the water contained therein by distillation (8), this water being used optionally for washing (6.0) that proportion of the organic phase (D) leaving extraction stage (3) fed to working-up by distillation (6.1), (6.2), and/or for washing (7.0) that proportion of the organic phase (L) leaving extraction stage (5) fed to working-up by distillation (7.1) for the purpose of removing acid traces and the water (Y) obtained in so doing is returned to the aqueous phase at a suitable place.

5. The process of claim 2, wherein f) a partial quantity (D") of the organic phase (D) leaving extraction stage (3) is separated and extracted countercurrently in an upstream, preferably multistage, extraction stage (2) with at least a partial quantity, preferably with the entire stream of (C) and the partial stream (D") is calculated in such a manner that the polyamine contained in (D") is as far as possible transferred into the aqueous phase leaving the extraction unit (2), the said aqueous phase, optionally after the addition of water from stream (Y) and/or auxiliary amine and/or further aqueous phase from stream (C) is introduced into extraction stage (3) and the organic phase (R) arising in (2), which is substantially composed of hydrophobic solvent and optionally auxiliary amine, is also introduced into extraction stage (3) and, as a constituent of the organic phase (B), is used as a solvent for the starting polyamine (A).

6. The process of claim 2, wherein the auxiliary amine used is aniline.

7. The process of claim 2, wherein the polyamine mixture used is a polyamine mixture of the diphenylmethane series obtained during acid-catalyzed aniline/formaldehyde condensation.

8. In a process for the preparation of aromatic polyisocyanates by phosgenating an aromatic polyamine, the improvement wherein the aromatic polyamine is produced by the process of claim 1.

9. In a process for the preparation of cycloaliphatic polyamines by hydrogenating aromatic polyamines, the improvement wherein the aromatic polyamines are produced by the process of claim 1.

* * * * *